United States Patent
Duffy et al.

(10) Patent No.: US 12,351,541 B2
(45) Date of Patent: *Jul. 8, 2025

(54) PROCESS FOR PREPARING CYANOACETATES

(71) Applicant: Henkel AG & Co. KGaA, Duesseldorf (DE)

(72) Inventors: Cormac Duffy, County Louth (IE); Justine O'Sullivan, County Kildare (IE); Ciara Goff, County Wexford (IE); Umar Farid, County Dublin (IE); Jessica Ramos, County Kildare (IE); Michael Thai Trung King, Dublin (IE); Isidro Cobo Cardenete, Dublin (IE); Marisa Phelan, Dublin (IE); Barry Burns, Dublin (IE)

(73) Assignee: Henkel AG & Co. KGaA, Duesseldorf (DE)

( * ) Notice: Subject to any disclaimer, the term of this patent is extended or adjusted under 35 U.S.C. 154(b) by 724 days.

This patent is subject to a terminal disclaimer.

(21) Appl. No.: 17/503,914

(22) Filed: Oct. 18, 2021

(65) Prior Publication Data

US 2022/0033353 A1 Feb. 3, 2022

Related U.S. Application Data

(63) Continuation of application No. PCT/EP2020/060882, filed on Apr. 17, 2020.

(51) Int. Cl.
*C07C 253/30* (2006.01)
*C07C 253/34* (2006.01)

(52) U.S. Cl.
CPC .......... *C07C 253/30* (2013.01); *C07C 253/34* (2013.01)

(58) Field of Classification Search
CPC .................................................... C07C 253/30
See application file for complete search history.

(56) References Cited

U.S. PATENT DOCUMENTS

2022/0033350 A1* 2/2022 Duffy ................... C07C 253/34

OTHER PUBLICATIONS

Wu et al., Tetrahedron: Asymmetry (2003), 14(15), 2133-2142. (Year: 2003).*
Greenlee WJ, Thorsett ED. Mild conversion of carboxamides and carboxylic acid hydrazides to acids and esters. The Journal of Organic Chemistry. Dec. 1981;46(26):5351-3.
Ouwerkerk N, Boom JV, Lugtenburg J, Raap J. Synthesis of [1', 2', 5', 2-13C4]-2'-Deoxy-d-adenosine by a Chemoenzymatic Strategy to Enable Labelling of Any of the 215 Carbon-13 and Nitrogen-15 Isotopomers. European Journal of Organic Chemistry. Jul. 2002;2002(14):2356-62.
Fundamentals of University Organic Chemistry, Part II, the second edition, edited by RONG Guobin, p. 459, East China University of Science and Technology Press, published in Aug. 2006.

* cited by examiner

*Primary Examiner* — Laura L Stockton
(74) *Attorney, Agent, or Firm* — Steven C. Bauman

(57) ABSTRACT

This invention relates to a process for producing cyanoacetates using a cyanoacetamide as a precursor.

15 Claims, No Drawings

PROCESS FOR PREPARING CYANOACETATES

BACKGROUND

Field

This invention relates to a process for producing cyanoacetates using a cyanoacetamide as a precursor.

Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251. Thus, it is seen one use of cyanoacetates is in the formation of cyanoacrylates.

Vijayalakshmi et al., *J. Ad. Sci. Technol.*, 4, 9, 733 (1990) describes some approaches to the synthesis of cyanoacetates and corresponding cyanoacrylates, including preparation from chloroacetic acid and its esters by subsequent reaction with sodium cyanide.

Guseva et al., *Russia Chem. Bull.*, 42, 3, 478 (1993) describes functionalized cyanoacetates, many of which were used in the subsequent synthesis of corresponding cyanoacrylates. [See also Guseva et al., *Russia Chem. Bull.*, 43, 4, 595 (1994), and Golobolov and Gruber, *Russia Chem. Rev.*, 66, 11, 953 (1997).] Cyanoacetates with siliconised functionalities have been described. See e.g. Senchenya et al., *Russia Chem. Bull.*, 42, 5, 909 (1993) and European Patent Document No. EP 0 459 617.

The preparation of mono-, di-, tri- and tetra-functional cyanoacetates, albeit as curatives for epoxy resins for adhesive applications, has been described. Renner et al., "Cure of Epoxy Resins with Esters of Cyanoacrylic Acid", *J. Polym. Sci., Polym. Chem. Ed.*, 23, 2341 (1985) and U.S. Pat. Nos. 4,202,920 and 4,512,357.

Notwithstanding the state of the technology it would be desirable to find alternative synthetic approaches to making cyanoacetates, particularly if such approaches used readily available and inexpensive starting materials. It would be even more desirable if such approaches generated the subject cyanoacetate in high yield, was readily isolated, and used at least starting materials that are recognized as being safe.

SUMMARY

At a high level, the inventive process provides for the preparation of a cyanoacetate, steps of which comprise:

(a) contacting a cyanoacetamide with an alcohol, in the presence of a mineral acid, under appropriate conditions and for a time sufficient to yield a cyanoacetate;

(b) optionally, separating therefrom the so formed cyanoacetate.

The separation step should yield the cyanoacetate substantially free from the cyanoacetamide, the alcohol, mineral acid, and by-products.

DETAILED DESCRIPTION

As noted above, the present invention provides a process for the preparation of a cyanoacetate, steps of which comprise:

(a) contacting a cyanoacetamide with an alcohol, in the presence of a mineral acid, under appropriate conditions and for a time sufficient to yield a cyanoacetate;

(b) optionally, separating therefrom the so formed cyanoacetate.

The separation step should yield the cyanoacetate substantially free from the cyanoacetamide, the alcohol, mineral acid, and by-products.

The cyanoacetate formed by the inventive process may be a $C_{1-20}$ alkyl cyanoacetate, a $C_{6-20}$ aryl cyanoacetate, a $C_{7-20}$ alkaryl cyanoacetate or a $C_{7-20}$ aralkyl cyanoacetate, any of which may be substituted by one or more hydroxyl groups or $C_{1-20}$ alkyl ether groups.

More specifically, the cyanoacetate may be a $C_{1-20}$ alkyl cyanoacetate, where the $C_{1-20}$ alkyl may be straight chain or branched, contain one or more points of unsaturation and may be substituted and/or interrupted by one or more heteroatoms or heteroatom-containing groups (such as trimethylsilyl alkyl, like methyl, ethyl or propyl), or substituted by halogens or substituted or interrupted by halogen-containing groups. For instance, the cyanoacetate may be methyl, ethyl, propyls (like n-propyl or iso-propyl), propargyl, butyls (like n-butyl or iso-butyl), pentyls (like n-pentyl or iso-amyl), hexyl, octyls (like n-octyl or 2-ethylhexyl), nonyl, oxononyl, decyl, dodecyl, allyl, ethynyl, butenyl, cyclohexyl, tetrahydrofurfuryl, chloroethyl, 2,2,2-trifluoroethyl, hexafluoroisopropyl, alkoxy ether alkyl cyanoacetates (such as methoxymethyl, methoxyethyl, methoxybutyl, ethoxyethyl, propoxyethyl, butoxymethyl, or butoxyethyl) and dimethyl siloxane esters of 2-cyanoacetic acid. This recitation is by no means however exhaustive.

Desirably, the so formed cyanoacetate should be a $C_{1-20}$ alkyl cyanoacetate selected from methyl cyanoacetate, ethyl cyanoacetate, propyl cyanoacetates, butyl cyanoacetates, pentyl cyanoacetates, octyl cyanoacetates, alkoxy ether alkyl cyanoacetates, allyl cyanoacetates, and combinations thereof.

The cyanoacetate may also be a $C_{6-20}$ aryl cyanoacetate such as phenyl cyanoacetate.

Or, the cyanoacetate may be a $C_{7-20}$ aralkyl cyanoacetate such as phenethyl cyanoacetate, benzyl cyanoacetate, and toluyl cyanoacetate, to name a few.

In conducting the process, a cyanoacetamide is the starting material or precursor to the cyanoacetate.

The cyanoacetamide may be cyanoacetamide itself or a derivative thereof. Cyanoacetamide derivatives include mono- or di-substituted cyanoacetamides, where the substitutions may be alkyl, alkenyl, alkynyl or aryl. For instance, alkyl substituted cyanoacetamides include methyl, ethyl, propyl, or butyl substituted cyanoacetamides; aryl substituted cyanoacetamides include phenyl or benzyl cyanoacetamides. The substituted cyanoacetamides may further have halogen or hydroxyl substitution thereon. Commercially available examples of such cyanoacetamide derivatives include N,N-diethyl-2-cyanoacetamide, for instance.

The cyanoacetamide should be used in an amount of about 1 equivalent against which the other reactants may be measured. The term "equivalent" is intended to capture molar equivalent, whenever it is used herein.

An alcohol is used to perform the esterification of step (a). The alcohol chosen may be an alkyl alcohol, an aryl alcohol, an alkaryl alcohol or an aralkyl alcohol. The identity of the chosen alcohol depends on the desired cyanoacetate sought to be prepared. Accordingly, the alcohol may be selected from methanol, ethanol, propanols (such as isopropanol), proparganols, butanols (such as isobutanol), pentanols (such as isoamyl alcohol), hexanols, octanols, nonanols, oxononanols, decanols, dodecanols, allanol, cyclohexanol, tetrahydrofurfurol, chloroethanol, 2,2,2-trifluoroethanol, hexafluoroisopropanol, alkoxy ether alkanols (such as methoxymethanol, methoxyethanol, methoxybutanol, ethoxyethanol, propoxyethanol, butoxymethanol, or butoxyethanol), dialkyl siloxanols (such as dimethyl siloxanol or diethyl siloxanol), trialkylsilylalkanols (such as trimethylsilylmethanol, trimethylsilylethanol or trimethylsilylpropanol), should the corresponding respective alkyl cyanoacetate ester sought to be produced. Or, if the chosen alcohol is an aromatic alcohol, such as phenol, benzyl alcohol or derivatives thereof, then the corresponding aryl cyanoacetate ester would be the desired product.

The alcohol should be used in an amount of about 2.5 to about 25 equivalents, such as about 5 to about 10 equivalents, desirably about 5 to about 7.5 equivalents.

The mineral acid used in the inventive process may be selected from sulfuric acid, sulfurous acid, sulfonic acid, phosphoric acid, phosphorous acid, phosphoric acid, hydrochloric acid or hydrobromic acid.

The mineral acid should be used in an amount of about 0.5 to about 1.5 equivalents to about 1 equivalent of a cyanoacetamide, such as in an amount of about 0.6 to about 1.2 equivalents to about 1 equivalent of the cyanoacetamide, desirably about 0.6, about 0.9 or about 1.2 equivalents to about 1 equivalent of the cyanoacetamide starting material.

The alcohol should be used in excess to either or both of the cyanoacetamide and the mineral acid.

In the inventive process, the cyanoacetate is formed in a yield of about 70% or greater, such as about 90% or greater.

While the time of reaction is generally given above, the time may be monitored by reference to the formation of the desired product using NMR spectrometry, as noted in the Examples. The time of reaction may be adjusted depending on the identity of the specific reactants, the scale of the reaction and whether heat is added to the reaction conditions.

For the optional step of (b) appropriate isolation and/or separation techniques may be used to obtain the cyanoacetate.

The following examples are intended to illustrate but in no way limit the present invention.

Examples

We used reaction conditions reported in Z.-L. Wu et al., Tetrahedron: Asymmetry, 14, 2133-42 (2003) to esterify the amide of a cyanoacetamide, along the synthetic scheme set forth below:

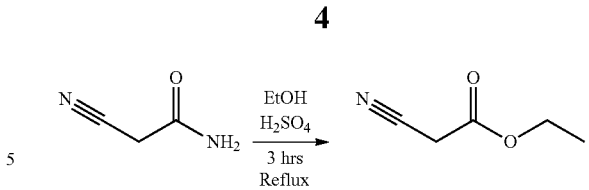

Applying the synthesis conditions of Z.-L. Wu the ethyl ester of cyanoacetate was obtained. The yields varied, as shown below in Table. The sulfuric acid equivalents were varied as was the time of reaction in the last instance. Table 1 below shows each of the six entries, all having 1 equivalent of the cyanoacetamide (30 grams) and 5.75 equivalents of ethanol (94.5 grams).

TABLE 1

| Entry | $H_2SO_4$ (eq) | Time (hrs) | Yield (%) |
|---|---|---|---|
| 1 | 0.3 | 3 | 41 |
| 2 | 0.15 | 3 | 12 |
| 3 | 0.6 | 3 | 69 |
| 4 | 1.2 | 3 | 94 |
| 5 | 0.9 | 3 | 97 |
| 6 | 0.3 | 17 | 32 |

From Entries 3-5, it may be seen that only those having about 70% or higher are within the scope of the inventive process. Thus, the mineral acid range of about 0.6 to about 1.2 is seen to be significant in order to obtain the desired yields.

Confirmation of formation of the ethyl cyanoacetate was obtained by NMR spectral analyses.

What is claimed is:
1. A process for the preparation of a cyanoacetate, steps of which comprise:
   (a) contacting cyanoacetamide with an alcohol, in the presence of a mineral acid, under appropriate conditions and for a time sufficient to yield a cyanoacetate; and
   (b) optionally, separating therefrom the so formed cyanoacetate, wherein the cyanoacetate is a $C_{1-20}$ alkyl cyanoacetate, a $C_{6-20}$ aryl cyanoacetate, a $C_{7-20}$ alkaryl cyanoacetate or a $C_{7-20}$ aralkyl cyanoacetate, any of which may be substituted by one or more hydroxyl groups or $C_{1-20}$ alkyl ether groups.
2. The process of claim 1, wherein the cyanoacetate is a $C_{1-20}$ alkyl cyanoacetate selected from methyl cyanoacetate, ethyl cyanoacetate, propyl cyanoacetates, butyl cyanoacetates, pentyl cyanoacetates, octyl cyanoacetates, alkoxy ether alkyl cyanoacetates, allyl cyanoacetate, and combinations thereof.
3. The process of claim 1, wherein the cyanoacetate is a $C_{6-20}$ aryl cyanoacetate.
4. The process of claim 1, wherein the cyanoacetate is a $C_{7-20}$ aralkyl cyanoacetate.
5. The process of claim 1, wherein the alcohol is an alkyl alcohol, an aryl alcohol, an alkaryl alcohol or an aralkyl alcohol.
6. The process of claim 1, wherein the alcohol is selected from methanol, ethanol, propanols, proparganols, butanols, pentanols, hexanols, octanols, nonanols, oxononanols, decanols, dodecanols, allanol, cyclohexanol, tetrahydrofurfurol, chloroethanol, 2,2,2-trifluoroethanol, hexafluoroisopropanol, alkoxy ether alkanols, dialkyl siloxanols, or trialkylsilylalkanols.

7. The process of claim 1, wherein the alcohol is an aromatic alcohol.

8. The process of claim 1, wherein the alcohol is selected from phenol, benzyl alcohol or derivatives thereof.

9. The process of claim 1, wherein the mineral acid is sulfuric acid, sulfurous acid, sulfonic acid, phosphoric acid, phosphorous acid, phosphonic acid, hydrochloric acid or hydrobromic acid.

10. The process of claim 1, wherein the alcohol is used in excess to either or both of the cyanoacetamide and the mineral acid.

11. The process of claim 1, wherein the cyanoacetate is formed in an amount of about 90% or greater.

12. The process of claim 1, wherein step (b) is free from the cyanoacetamide, mineral acid, and/or alcohol, and by-products.

13. The process of claim 1, wherein the cyanoacetate is phenyl cyanoacetate.

14. The process of claim 1, wherein the cyanoacetate is selected from phenethyl cyanoacetate, benzyl cyanoacetate, or toluyl cyanoacetate.

15. The process of claim 1, wherein the alcohol is present in an amount of from 2.5 equivalents to 10 equivalents, per equivalent of cyanoacetamide; and wherein the mineral acid is present in an amount of from 0.6 equivalents to 1.2 equivalents per equivalent of cyanoacetamide; wherein the cyanoacetate is formed in an amount of about 70% or greater.

\* \* \* \* \*